(12) United States Patent
Hayakawa et al.

(10) Patent No.: US 12,162,740 B2
(45) Date of Patent: Dec. 10, 2024

(54) CONTAINER STERILIZING DEVICE, CONTENT FILLING SYSTEM, CONTAINER STERILIZING METHOD, AND CONTENT FILLING METHOD

(71) Applicant: Dai Nippon Printing Co., Ltd., Tokyo (JP)

(72) Inventors: Atsushi Hayakawa, Tokyo (JP); Yuiko Wada, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 86 days.

(21) Appl. No.: 17/310,901

(22) PCT Filed: Feb. 21, 2020

(86) PCT No.: PCT/JP2020/007240
§ 371 (c)(1),
(2) Date: Aug. 30, 2021

(87) PCT Pub. No.: WO2020/179521
PCT Pub. Date: Sep. 10, 2020

(65) Prior Publication Data
US 2022/0127125 A1    Apr. 28, 2022

(30) Foreign Application Priority Data

Mar. 1, 2019   (JP) .................................. 2019-037645

(51) Int. Cl.
*B67C 7/00*           (2006.01)

(52) U.S. Cl.
CPC .......... *B67C 7/0073* (2013.01); *B67C 7/0013* (2013.01); *B67C 7/004* (2013.01)

(58) Field of Classification Search
CPC ..... B67C 7/0073; B67C 7/0013; B67C 7/004; B65B 39/003; B65B 2039/009; B65B 39/14; B65B 39/145; B65B 51/16
(Continued)

(56) References Cited

U.S. PATENT DOCUMENTS 4,326,568 A * 4/1982 Burton .................. B65B 39/145
                                                    141/144
6,119,440 A * 9/2000 Benner, Jr. ............ B65B 39/145
                                                    53/473
(Continued)

FOREIGN PATENT DOCUMENTS

CN          1336829 A       2/2002
CN        105658526 A       6/2016
(Continued)

OTHER PUBLICATIONS

English translation of the International Preliminary Report on Patentability (Chapter I) dated Sep. 16, 2021 (Application No. PCT/JP2020/007240).
(Continued)

*Primary Examiner* — Sameh Tawfik
(74) *Attorney, Agent, or Firm* — BURR PATENT LAW, PLLC

(57) ABSTRACT

A container sterilizing device includes a transport mechanism that transports a container and a supply unit that supplies a sterilizing agent to the container that is being transported by the transport mechanism. The supply unit includes a nozzle for spraying the sterilizing agent. The nozzle does not move in a vertical direction and, without being inserted into the container, moves in synchronization with the container that is being transported by the transport mechanism.

6 Claims, 11 Drawing Sheets

(58) Field of Classification Search
USPC .......................................... 53/425; 253/425
See application file for complete search history.

(56) References Cited

U.S. PATENT DOCUMENTS

| | | | |
|---|---|---|---|
| 11,203,514 B2* | 12/2021 | Kuwano | ............... B67C 7/0073 |
| 2004/0208781 A1 | 10/2004 | Hayashi et al. | |
| 2010/0021359 A1 | 1/2010 | Auer et al. | |
| 2011/0094616 A1* | 4/2011 | Hayakawa | .............. B67C 3/242 |
| | | | 141/85 |
| 2016/0121376 A1* | 5/2016 | Hayakawa | ........... B67C 7/0073 |
| | | | 422/3 |
| 2017/0290938 A1* | 10/2017 | Hayakawa | ................ A61L 2/04 |
| 2019/0218088 A1 | 7/2019 | Hayakawa | |

FOREIGN PATENT DOCUMENTS

| | | |
|---|---|---|
| EP | 3 428 077 A1 | 1/2019 |
| JP | 2008-100130 A | 5/2008 |
| JP | 4526820 B2 | 8/2010 |
| JP | 4700946 B2 | 6/2011 |
| JP | 5332603 B2 | 11/2013 |

OTHER PUBLICATIONS

Extended European Search Report dated Oct. 20, 2022 (Application No. 20766467.3).
Chinese Office Action (with English translation) dated Sep. 1, 2022 (Application No. 202080012177.7).
Japanese Office Action (Application No. 2019-037645) dated Mar. 13, 2020 (with English translation).
Japanese Office Action (Application No. 2019-037645) dated Aug. 18, 2020 (with English translation).
International Search Report and Written Opinion (Application No. PCT/JP2020/007240) dated May 26, 2020.

* cited by examiner

CONTAINER STERILIZING DEVICE, CONTENT FILLING SYSTEM, CONTAINER STERILIZING METHOD, AND CONTENT FILLING METHOD

TECHNICAL FIELD

The present disclosure relates to a container sterilizing device, a content filling system, a container sterilizing method, and a content filling method.

BACKGROUND ART

An aseptic filling system that fills a sterilized container (plastic bottle) with a sterilized content in an aseptic environment and then closes the container with a cap is known. To be specific, in the aseptic filling system, a molded container is supplied to the aseptic filling system, and hydrogen peroxide aqueous solution as a sterilizing agent is sprayed to the container in the aseptic filling system. Subsequently, the container is dried to be sterilized, and then the container is aseptically filled with a content.

As a method of sterilizing a container, a sterilizing method in which a sterilizing agent is sprayed from the mouth of the container while inserting a nozzle into the container, and a sterilizing method in which a sterilizing agent is supplied to the inner surface and the outer surface of the container without inserting a nozzle into the container are known (see, for example Patent Literatures 1 and 2).

However, as described in Patent Literature 1, in the sterilizing method that sterilizes a container while inserting a nozzle into a container, it is necessary to move the nozzle up and down in order to insert the nozzle into the container. Therefore, the sterilizing method has a problem in that it takes a long operation time to perform a step of supplying the sterilizing agent and the cost of a sterilizing device is high. In recent years, reduction in weight of a container has been demanded, and the thickness of the wall of the container has decreased. Therefore, when a sterilizing agent is sprayed to a container having a thin wall while inserting a nozzle into the container, the container may deform due to heat of the sterilizing agent.

As described in Patent Literature 2, with the sterilizing method in which the sterilizing agent is supplied to the inner surface and the outer surface of the container without inserting a nozzle into the container, there is a case where it is difficult to efficiently supply the sterilizing agent to the inner surface of the container. In this case, a problem arises in that it is necessary to increase the amount of the sterilizing agent used, in order to efficiently supply the sterilizing agent to the inner surface of the container.

As described in Patent Literature 3, there is a method in which heat applied to a bottle due to blow molding is used for sterilization. However, the cost of the method is high because it is necessary to provide temperature adjusting equipment for adjusting the temperature of the bottle, and it is necessary to measure the temperature of the bottle because heat after blow molding is one of the sterilizing factors.

CITATION LIST

Patent Literature

[Patent Literature 1] Japanese Patent No. 4526820
[Patent Literature 2] Japanese Patent No. 4700946
[Patent Literature 3] Japanese Patent No. 5332603

The present disclosure has been made in consideration of such points, and an object of the present disclosure is to provide a container sterilizing device, a content filling system, a container sterilizing method, and a content filling method with each of which it is possible to reduce the cost of a sterilizing device and to efficiently supply a sterilizing agent to a container.

DISCLOSURE OF INVENTION

An embodiment of the present disclosure is a container sterilizing device including: a transport mechanism that transports a container; and a supply unit that supplies a sterilizing agent to the container that is being transported by the transport mechanism. The supply unit includes a nozzle for spraying the sterilizing agent. The nozzle does not move in a vertical direction and, without being inserted into the container, moves in synchronization with the container that is being transported by the transport mechanism.

In an embodiment of the present disclosure, the supply unit may further include a fixed cover that includes an inlet through which the sterilizing agent flows into the fixed cover, and a rotary plate that holds the nozzle and that is rotatably provided in the fixed cover; and a sealing member may be interposed between the fixed cover and the rotary plate.

In an embodiment of the present disclosure, a fixed shield plate that has an opening formed along a transport path of the container may be interposed between the fixed cover and the rotary plate.

An embodiment of the present disclosure is a content filling system including: the container sterilizing device according to the present disclosure; a filling device that fills the container with a content; and a cap attachment device that closes the container with a cap.

An embodiment of the present disclosure is a container sterilizing method including: a transport step of transporting a container by using a transport mechanism; and a sterilizing-agent supplying step of supplying a sterilizing agent to the container that is being transported by the transport mechanism by using a supply unit including a nozzle for spraying the sterilizing agent. In the sterilizing-agent supplying step, the nozzle does not move in a vertical direction and, without being inserted into the container, supplies the sterilizing agent to the container while moving in synchronization with the container that is being transported by the transport mechanism.

In an embodiment of the present disclosure, the supply unit may include a fixed cover that includes an inlet through which the sterilizing agent flows into the fixed cover, and a rotary plate that holds the nozzle and that is rotatably provided in the fixed cover; and a sealing member may be interposed between the fixed cover and the rotary plate.

In an embodiment of the present disclosure, a fixed shield plate that has an opening formed along a transport path of the container may be interposed between the fixed cover and the rotary plate.

An embodiment of the present disclosure is a content filling method including: a step of sterilizing a container by using the container sterilizing method according to the present disclosure; a step of filling the container with a content; and a step of closing the container with a cap.

With the present disclosure, it is possible to reduce the cost of a sterilizing device, and it is possible to efficiently supply a sterilizing agent to a container.

DESCRIPTION OF EMBODIMENTS

Hereafter, embodiments of the present invention will be described with reference to the drawings. FIGS. 1 to 8 illustrate an embodiment of the present invention.

Content Filling System

First, referring to FIG. 1, a content filling system (aseptic filling system) according to the embodiment will be described.

Figure 1:
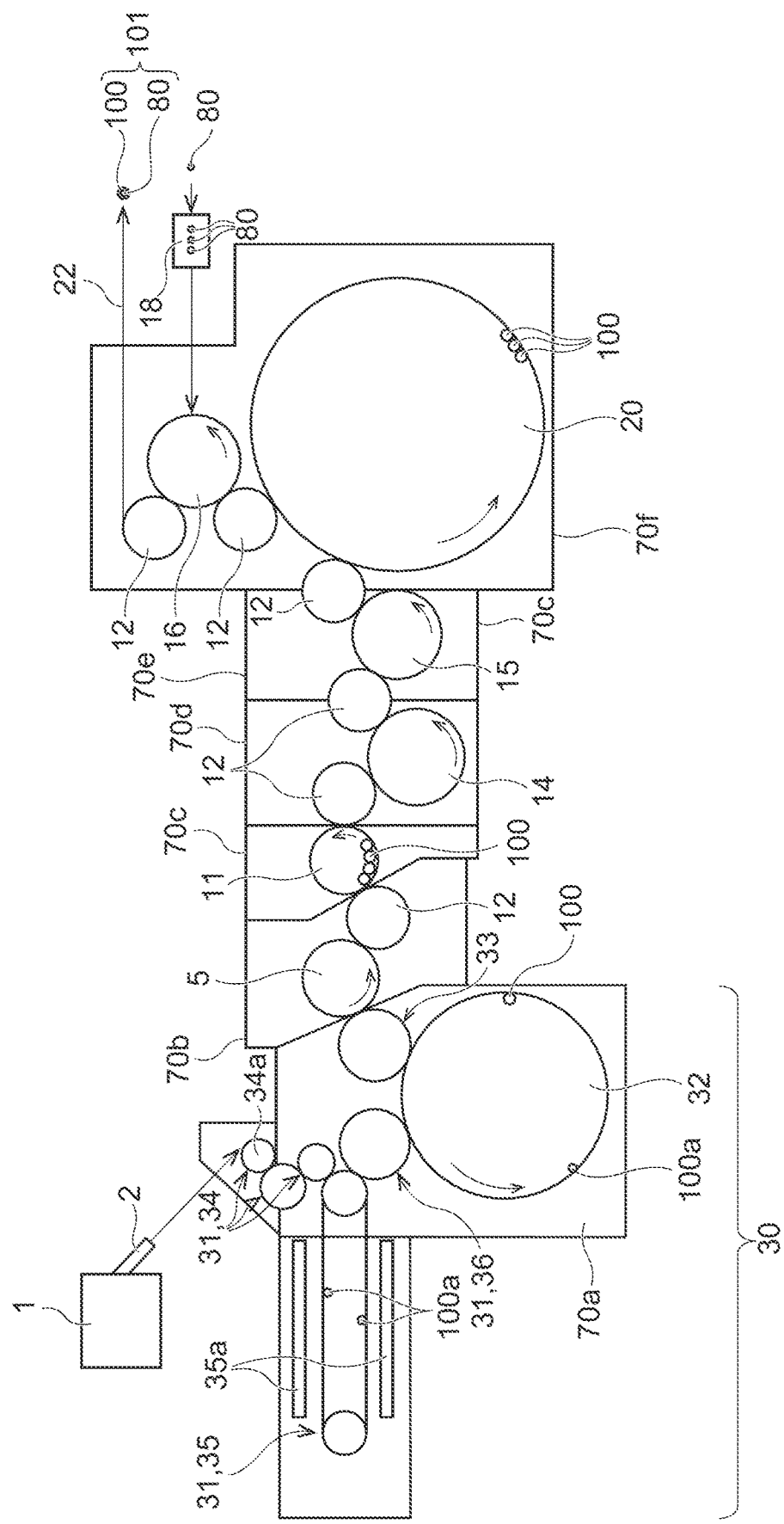
FIG. 1 is a schematic plan view illustrating a content filling system according to the present embodiment.

FIG. 1 illustrates a content filling system 10 that fills a bottle 100 (container) with a content such as a beverage. The bottle 100 can be made by biaxial-stretch blow-molding a preform that has been made by injection-molding a synthetic resin material. Preferably, a thermoplastic resin, in particular, polyethylene (PE), polypropylene (PP), polyethylene terephthalate (PET), or polyethylene naphthalate (PEN) is used as the material of the bottle 100. In addition, the container may be a glass container, a can, a paper container, a pouch, or a combined container of any of these. In the present embodiment, a case where a bottle is used as the container will be described as an example.

As illustrated in FIG. 1, the content filling system 10 includes a bottle molding section 30, a sterilizing device 11 (container sterilizing device), an air rinse device 14, an aseptic-water rinse device 15, a filling device 20 (filler), a cap attachment device 16 (a capper, a seamer, and a capping machine), and a product-bottle discharge section 22. The bottle molding section 30, the sterilizing device 11, the air rinse device 14, the aseptic-water rinse device 15, the filling device 20, the cap attachment device 16, and the product-bottle discharge section 22 are arranged in this order from the upstream side toward the downstream side in the transport direction of the bottle 100. A plurality of transport wheels 12 that transport the bottle 100 between these devices are provided between an adjustment transport unit 5 (described below), the sterilizing device 11, the air rinse device 14, the aseptic-water rinse device 15, the filling device 20, and the cap attachment device 16.

The bottle molding section 30 successively receives a preform 100a from the outside, molds the bottle 100, and transports the molded bottle 100 toward the sterilizing device 11 to supply the molded bottle 100. Thus, because the bottle molding section 30 is configured to receive the preform 100a and to mold the bottle 100, the content filling system 10 can continuously perform a step of supplying the preform 100a, a step of molding the bottle 100, a step of filling the bottle 100 with a content, and a step of closing the bottle 100. In this case, the transport cost can be reduced, because, instead of the bottle 100 having a large volume, the preform 100a having a small volume can be transported from the outside to the content filling system 10.

The bottle molding section 30 includes a preform transport unit 31 that transports the preform 100a, a blow molding unit 32 that molds the bottle 100 by blow-molding the preform 100a, and a bottle transport unit 33 that transports the molded bottle 100.

The preform transport unit 31 includes a receiving portion 34 that receives the preform 100a that is supplied from a preform supply device 1 via a preform supply conveyor 2, a heating portion 35 that receives the preform 100a from the receiving portion 34 and heats the preform 100a while transporting the preform 100a, and a transfer portion 36 that receives the preform 100a that has been heated by the heating portion 35 and transfers the preform 100a to the blow molding unit 32. In the receiving portion 34, a preform sterilizing device 34a for sterilizing the preform 100a is provided. The preform sterilizing device 34a blows mist or gas of hydrogen peroxide aqueous solution to the preform 100a to sterilize the preform 100a (preliminary sterilization). The sterilizing agent for sterilizing the preform 100a may be any substance that can deactivate microorganisms. Examples of the sterilizing agent include hydrogen peroxide, peracetic acid, acetic acid, pernitric acid, nitric acid, a chlorine-based agent, sodium hydroxide, potassium hydroxide, alcohols such as ethyl alcohol and isopropyl alcohol, chlorine dioxide, ozone water, acid water, and a surface-active agent. One of these may be used, or a combination of two or more of these may be used.

The heating portion 35 includes a heater 35a that heats the preform 100a. The heater 35a may be, for example, an infrared heater. The heater 35a heats the preform 100a to a temperature of about 90° C. or higher and 130° C. or lower. The temperature of the mouth of the preform 100a is controlled to be 70° C. or lower, in order to prevent deformation and the like.

The blow molding unit 32 includes a die (not shown), and the bottle 100 is molded by blow-molding the preform 100a by using the die.

Between the bottle molding section 30 and the sterilizing device 11, the adjustment transport unit 5, which receives the bottle 100 from the bottle transport unit 33 of the bottle molding section 30 and transfers the bottle 100 to the sterilizing device 11, is provided. The adjustment transport unit 5 is accommodated in an atmosphere shut-off chamber 70b (described below). Thus, because the adjustment transport unit 5 is accommodated in the atmosphere shut-off chamber 70b, it is possible to suppress a failure such that gas or mist of the sterilizing agent or a mixture of these that is generated in a sterilizing-agent spraying chamber 70c (described below) flows into a molding section chamber 70a (described below) that accommodates the bottle molding section 30.

The sterilizing device 11 sterilizes the inside of the bottle 100 by ejecting the sterilizing agent to the bottle 100. Thus, the bottle 100 is sterilized by the sterilizing agent before the bottle 100 is filled with a content. As the sterilizing agent, for example, hydrogen peroxide aqueous solution is used. The sterilizing device 11 generates mist or gas of the hydrogen peroxide aqueous solution, and sprays the mist or gas to the inner and outer surfaces of the bottle 100. Because the bottle 100 is sterilized by the mist or gas of the hydrogen peroxide aqueous solution, the inner and outer surfaces of the bottle 100 are uniformly sterilized.

The air rinse device 14 supplies heated aseptic air or room-temperature aseptic air to the bottle 100, thereby removing foreign substances, hydrogen peroxide, and the like from the inside of the bottle 100 while activating hydrogen peroxide. As necessary, room-temperature aseptic air may be mixed with condensation mist of low-concentration hydrogen peroxide to gasify hydrogen peroxide, and the mixture may be supplied to the bottle 100. The configuration of the air rinse device 14 may be substantially the same as that of the sterilizing device 11 illustrated in FIG. 2 (described below).

The aseptic-water rinse device 15 cleans the bottle 100, which has been sterilized by hydrogen peroxide as a sterilizing agent, by using aseptic water having a temperature in the range of 15° C. to 85° C. Thus, hydrogen peroxide adhering to the bottle 100 is washed away, and foreign substances are removed.

The filling device 20 fills the inside of the bottle 100 with a content, which has been sterilized, from the mouth of the bottle 100. The filling device 20 fills the bottle 100 in an empty state with a content. The filling device 20 fills a plurality of bottles 100 with contents while the bottles 100 are rotated and transported.

The cap attachment device 16 closes the bottle 100 by attaching a cap 80 to the mouth of the bottle 100. The cap attachment device 16 closes the mouth of the bottle 100 with the cap 80 and tightly seals the mouth so that external air and microorganism may not enter the bottle 100. The cap attachment device 16 attaches the cap 80 to the mouth of each of a plurality of the bottles 100, which have been filled with contents, while the bottles 100 rotate (revolve). Thus, a product bottle 101 is obtained by attaching the cap 80 to the mouth of the bottle 100.

The cap 80 is sterilized beforehand by a cap sterilizing device 18. The cap sterilizing device 18 is disposed, for example, at a position that is outside of an aseptic chamber 70f (described below) and near the cap attachment device 16. The cap sterilizing device 18 gathers multiple caps 80, which have been transported from the outside of the content filling system 10, and transports the caps 80 toward the cap attachment device 16 in a row. While the caps 80 are being transported toward the cap attachment device 16, mist or gas of hydrogen peroxide is blown toward the inner and outer surfaces of the caps 80, and then the caps 80 are dried with hot air to be sterilized.

The product-bottle discharge section 22 continuously discharges the product bottle 101, to which the cap attachment device 16 has attached the cap 80, toward the outside of the content filling system 10.

The content filling system 10 includes the molding section chamber 70a, the atmosphere shut-off chamber 70b, the sterilizing-agent spraying chamber 70c, a first sterilizing-agent removing chamber 70d, a second sterilizing-agent removing chamber 70e, and the aseptic chamber 70f. The bottle molding section 30 is accommodated in the molding section chamber 70a, and the adjustment transport unit 5 is accommodated in the atmosphere shut-off chamber 70b. The sterilizing device 11 is accommodated in the sterilizing-agent spraying chamber 70c, the air rinse device 14 is accommodated in the first sterilizing-agent removing chamber 70d, and the aseptic-water rinse device 15 is accommodated in the second sterilizing-agent removing chamber 70e. The filling device 20, the cap sterilizing device 18, and the cap attachment device 16 described above are accommodated in the aseptic chamber 70f. The content filling system 10 may be, for example, an aseptic filling system. In this case, the inside of each of the sterilizing-agent spraying chamber 70c, the first sterilizing-agent removing chamber 70d, the second sterilizing-agent removing chamber 70e, and the aseptic chamber 70f is maintained in an aseptic state.

Alternatively, the content filling system 10 may be a high-temperature filling system that fills a container with a content in a high temperature of 85° C. or higher and lower than 100° C. The content filling system 10 may be an intermediate-temperature filling system that fills a container with a content in an intermediate temperature of 55° C. or higher and lower than 85° C.

Figure 2:
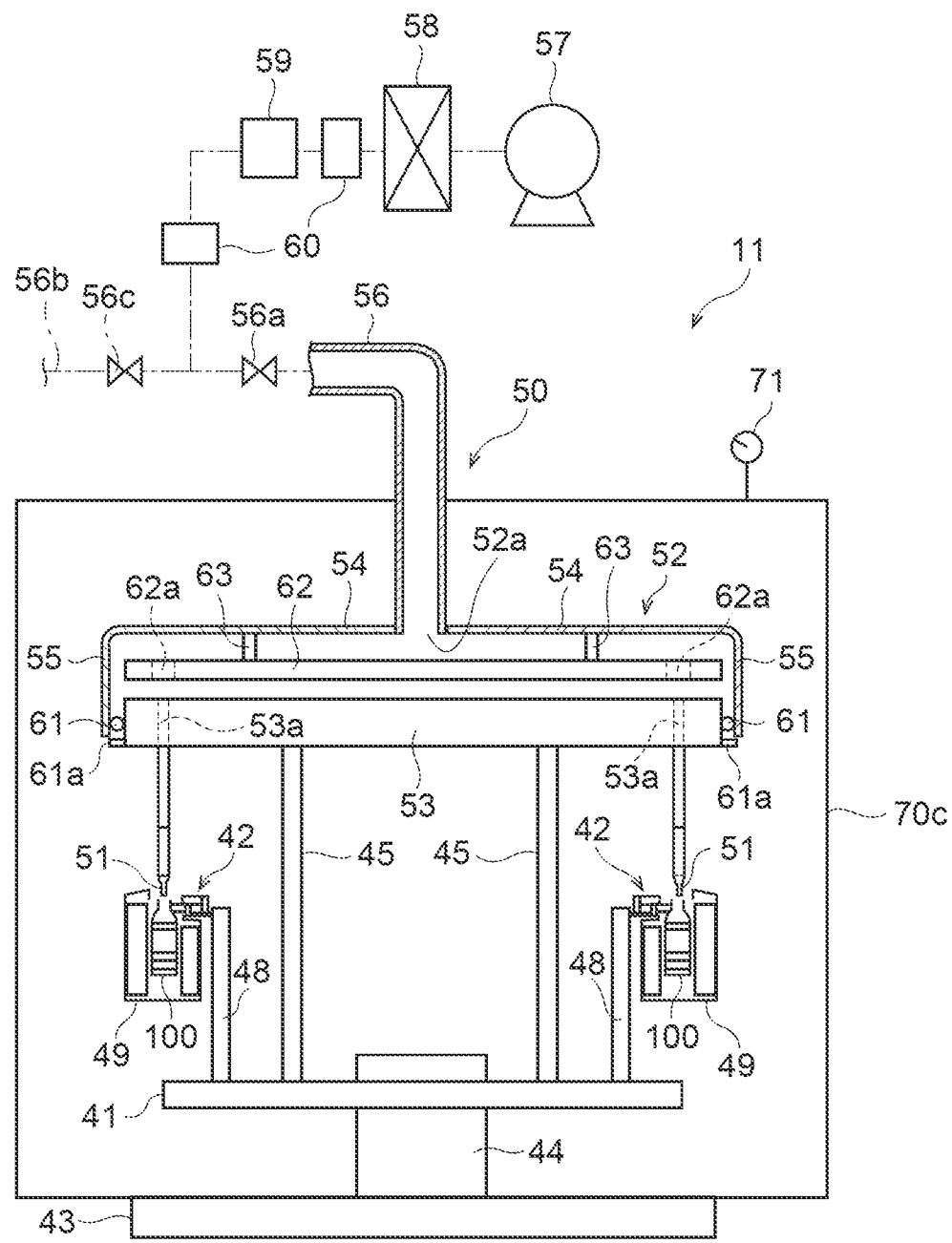
FIG. 2 is a schematic sectional view illustrating a container sterilizing device according to the present embodiment.

Next, referring to FIG. 2, the sterilizing device (container sterilizing device) according to the present embodiment will be described in detail. FIG. 2 is a schematic sectional view illustrating the sterilizing device 11. As illustrated in FIG. 2, the sterilizing device 11 includes a transport mechanism 40, and a supply unit 50 that supplies a sterilizing agent to the bottle 100 that is being transported by the transport mechanism 40. In the present embodiment, the transport mechanism 40 includes a wheel 41 that is rotatable, and a gripper 42 that is coupled to the wheel 41 and that transports the bottle 100 while holding the bottle 100.

The wheel 41 is configured to rotate by using driving force from a predetermined driving source, and is horizontally attached to a swiveling shaft 44 that stands on a base 43. Supporting poles 45 extend upward from a round surface of the wheel 41, and a rotary plate 53 (described below) of the supply unit 50 is coupled to the upper ends of the supporting poles 45.

Other supporting poles 48 extend upward from the round surface of the wheel 41, and grippers 42 for holding the bottles 100 are attached to upper parts of the supporting poles 48. Multiple supporting poles 48 and multiple grippers 42 are arranged at a predetermined pitch around the wheel 41. The multiple grippers 42 are coupled to the wheel 41 via the supporting poles 48 and rotate together with the wheel 41. A tunnel 49 is provided around the wheel 41 so as to surround the path of the bottles 100 held by the grippers 42. A sterilizing agent sprayed from a nozzle 51 (described below) is accumulated in the tunnel 49, and, as the bottle 100 passes through the tunnel 49, the outer surface of the bottle 100 is uniformly sterilized. It is possible to efficiently sterilize the outer surface of the bottle 100 by providing the tunnel 49. However, the tunnel 49 may be omitted. For example, it is possible to efficiently sterilize the outer surface of the bottle 100 by providing a camber wall between the wheel 41 and wheels that are disposed on both sides of the wheel 41 (in the example illustrated in FIG. 1, a wheel of the adjustment transport unit 5 and a wheel of the air rinse device 14, which are disposed on both sides of the sterilizing device 11) so that the camber wall forms a space having a small volume.

Next, the supply unit 50 of the sterilizing device 11 will be described. The supply unit 50 supplies the sterilizing agent to at least the inner surface of the bottle 100. The supply unit 50 may supply the sterilizing agent to the inner and outer surfaces of the bottle 100. The supply unit 50 includes the nozzle 51 for spraying the sterilizing agent, a fixed cover 52 including an inlet 52a through which the sterilizing agent flows into the fixed cover 52, and the rotary plate 53 that holds the nozzle 51 and that is rotatable provided in the fixed cover 52. The nozzle 51 does not move in the vertical direction and, without being inserted into the bottle 100, moves in synchronization with the bottle 100 that is being transported by the gripper 42 of the transport mechanism 40. In this case, the nozzle 51 is held by the rotary plate 53 so that an opening at the tip thereof directly faces the mouth of the bottle 100 held by the gripper 42. Thus, as the wheel 41 and the rotary plate 53 rotate, the nozzle 51 swivels around the swiveling shaft 44 together with the bottle 100 held by the gripper 42, and sprays the sterilizing agent to the bottle 100 while moving in synchronization with the bottle 100 that is being transported by the gripper 42 of the transport mechanism 40.

Figure 3:
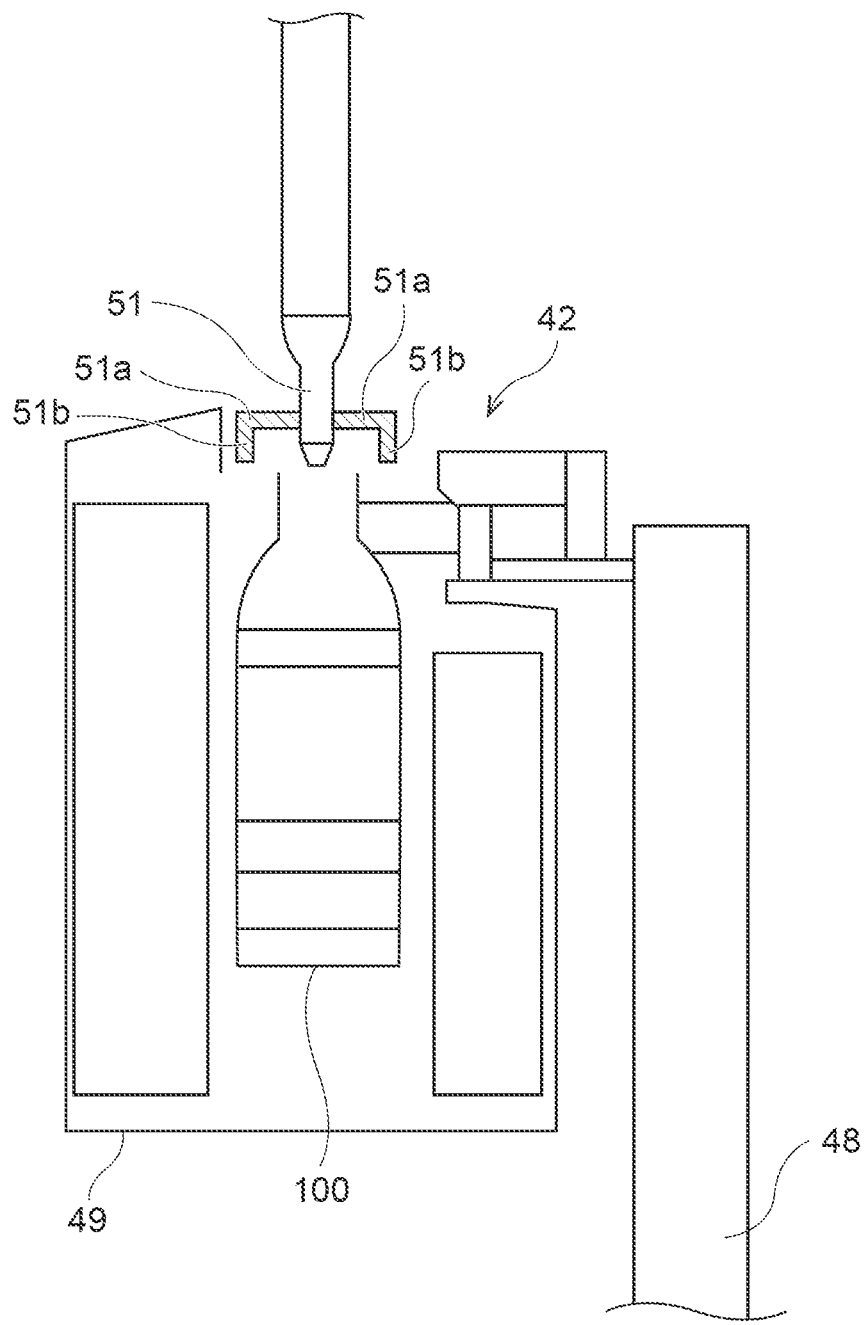
FIG. 3 is an enlarged schematic front view illustrating a nozzle of the container sterilizing device according to the present embodiment.

The inside diameter of the opening at the tip of the nozzle 51 may be 2 mm or larger and 10 mm or smaller, and preferably may be 3 mm or larger and 8 mm or smaller. When the inside diameter of the opening at the tip of the nozzle 51 is 2 mm or larger, it is possible to make the sterilizing agent, which is sprayed from the nozzle 51, efficiently adhere not only to the inner surface of the bottle 100 but also to the outer surface of the bottle 100. Therefore, it is possible to sterilize not only the inner surface of the bottle 100 but also the outer surface of the bottle 100. When the inside diameter of the opening at the tip of the nozzle 51 is 10 mm or smaller, it is possible to efficiently spray the sterilizing agent to the inner surface of the bottle 100, and it is possible to sterilize the bottle 100 while heating the bottle 100 to a desirable temperature as described below. The tip of the nozzle 51 may have a truncated-cone shape. In this case, as illustrated in FIG. 3, the nozzle 51 includes a flange 51a that is coaxial with the nozzle 51, and an annular wall 51b that protrudes from the periphery of the flange 51a toward the bottle 100. A nozzle having such a truncated-cone shape can guide a part of hot air that is supplied into the bottle 100 and that is blown out from the mouth to the outside of the bottle 100, toward the outer periphery of the mouth of the bottle 100. Thus, the mouth can be preheated and sterilized. Therefore, it is possible to efficiently and reliably sterilize a boundary portion between the outer surface and the inner surface of the bottle 100. In this case, preferably, the length of the nozzle 51 is 5 mm or larger and 200 mm or smaller. When the length of the nozzle 51 is 5 mm or larger, it is possible to appropriately maintain a driving force of sterilizing-agent gas. When the length of the nozzle 51 is 200 mm or smaller, it is possible to suppress condensation of gasified sterilizing agent due to decrease of temperature, and it is possible to effectively maintain a gas concentration that is necessary for bottle sterilization.

As illustrated in FIG. 2, the fixed cover 52 includes a top portion 54 having a substantially disc-like shape, and a side wall 55 that extends downward from the periphery of the top portion 54. The inlet 52a (described above) is formed in an upper central part of the top portion 54 of the fixed cover 52, and a conduit 56 is coupled to the inlet 52a. A valve 56a that controls flow of hydrogen peroxide gas in the conduit 56 is attached to the conduit 56.

On the upstream side of the conduit 56, a gas supply device, which is composed of a blower 57, a high efficiency particulate air (HEPA) filter 58, and an electric heater 59, are provided. A hydrogen-peroxide adding device 60 is installed on one or both of the upstream side and the downstream side of the electric heater 59. In a case where the hydrogen-peroxide adding device 60 is set on the downstream side of the electric heater 59, preferably, the hydrogen-peroxide adding device 60 mixes hydrogen peroxide in a gas phase into the pipe. If hydrogen peroxide is not in a gas phase, the residual value of hydrogen peroxide tends to increase. On the other hand, in a case where the hydrogen-peroxide adding device 60 is set on the upstream side of the electric heater 59, the hydrogen-peroxide adding device 60 may, for example, spray hydrogen peroxide in a liquid phase into the pipe. In this case, preferably, the temperature of the electric heater 59 is set to be the boiling point, or higher, of the sterilizing agent to be supplied but the temperature may be set to be 100° C. or higher (preferably, 130° C. or higher) in accordance with the degree to which the bottle 100 is to be sterilized. Another electric heater may be provided on the upstream side of the hydrogen-peroxide adding device 60, and the hydrogen-peroxide adding device 60 may spray hydrogen peroxide in a liquid phase to aseptic hot air (80° C. or higher). The hydrogen-peroxide adding device 60 may be installed on both of the upstream side and the downstream side of the electric heater 59. Here, if the material of the bottle 100 is polyethylene terephthalate (PET), hydrogen peroxide is easily adsorbed and the residual value tends increase; but, if the material is high-density polyethylene (HDPE), the adsorption amount of hydrogen peroxide is in the range of ⅕ to 1/20 and very small. Therefore, if the material of the bottle 100 is high-density polyethylene (HDPE), not only a method in which hydrogen peroxide solution is gasified and added to aseptic air but also a method in which hydrogen peroxide solution is sprayed to be mixed may be used. The hydrogen peroxide gas is supplied into the fixed cover 52 through the conduit 56, is blown out from the nozzle 51 to the bottle 100 via the rotary plate 53, and sterilizes the bottle 100. A pressure gauge 71 that measures the pressure of the inside of the sterilizing-agent spraying chamber 70c is attached to the sterilizing-agent spraying chamber 70c. The sterilizing agent may be any sterilizing agent that includes hydrogen peroxide of a concentration of 1% or higher. A 35% hydrogen peroxide solution diluted with ethanol may be used. When hydrogen peroxide is used as a sterilizing agent, a stabilizer included in the hydrogen peroxide component accumulates in the conduit 56. Therefore, in order to prevent blocking of the nozzle 51 by the stabilizer accumulated in the conduit 56, preferably, a structure that can cause water, an alkaline solution, an acid solution, or the like to flow to the supply unit 50 to perform cleaning in place (CIP) of the supply unit 50 is provided. In the illustrated example, a conduit 56b for CIP and a valve 56c that controls flow of a cleaning liquid in the conduit 56b is attached to the upstream side of the valve 56a. The conduit 56b for CIP may be attached to one or both of the upstream side and the downstream side of the hydrogen-peroxide adding device 60. Alternatively, the conduit 56b for CIP may be directly attached to the hydrogen-peroxide adding device 60.

The sterilizing agent may be any substance that can deactivate microorganisms. Examples of the sterilizing agent include hydrogen peroxide, ethanol, peracetic acid, acetic acid, pernitric acid, nitric acid, sodium hypochlorite, chlorine, and sodium hydroxide. One of these may be used, or a combination of two or more of these may be used.

As described above, the rotary plate 53 is coupled to the upper end of the supporting poles 45, and is rotatable together with the wheel 41 around the swiveling shaft 44. The rotary plate 53 has a substantially disc-like shape, and the rotary plate 53 has an opening 53a for supplying the sterilizing agent, which is supplied into the fixed cover 52, to the nozzle 51.

Figure 4:
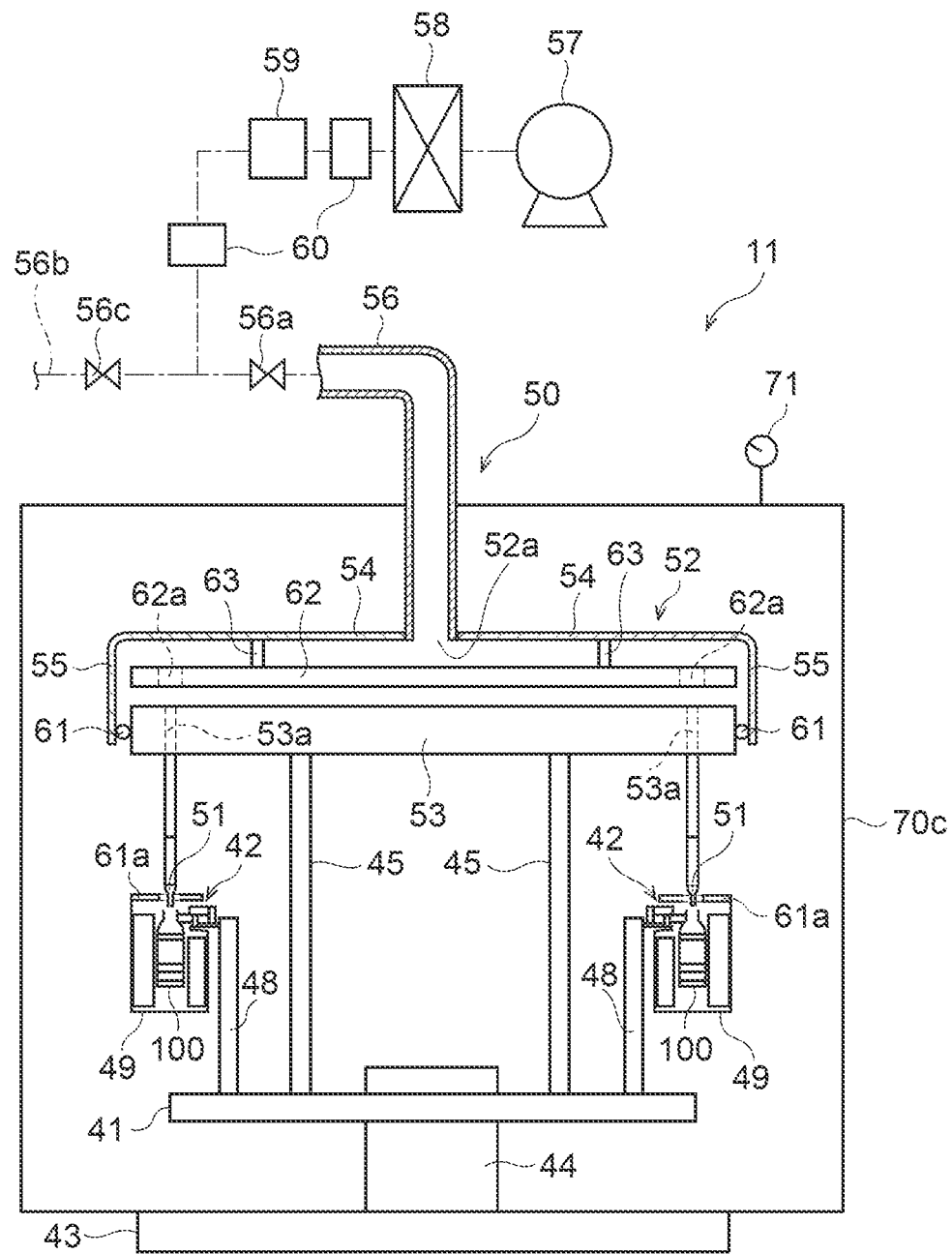
FIG. 4 is a schematic sectional view illustrating another example of the container sterilizing device according to the present embodiment.
Figure 5A:
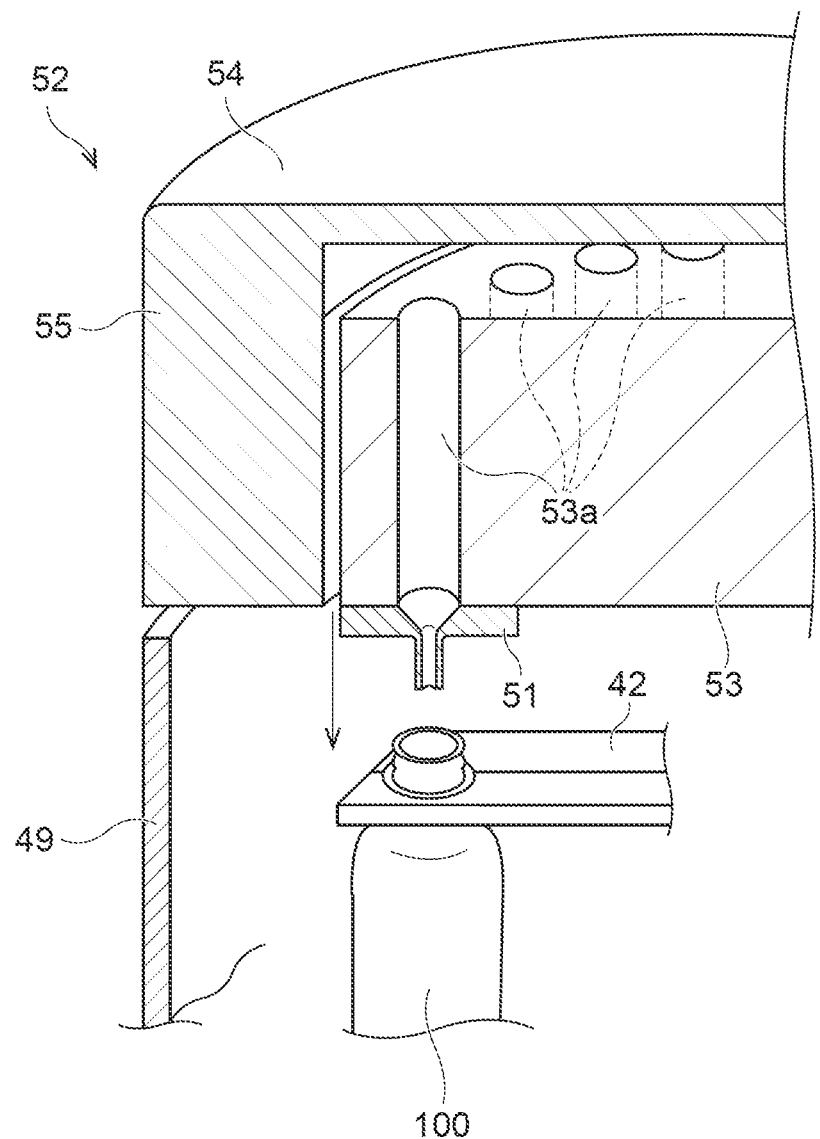
FIG. 5A is a schematic sectional view illustrating other examples of a fixed cover and a rotary plate of the container sterilizing device according to the present embodiment.
Figure 5B:
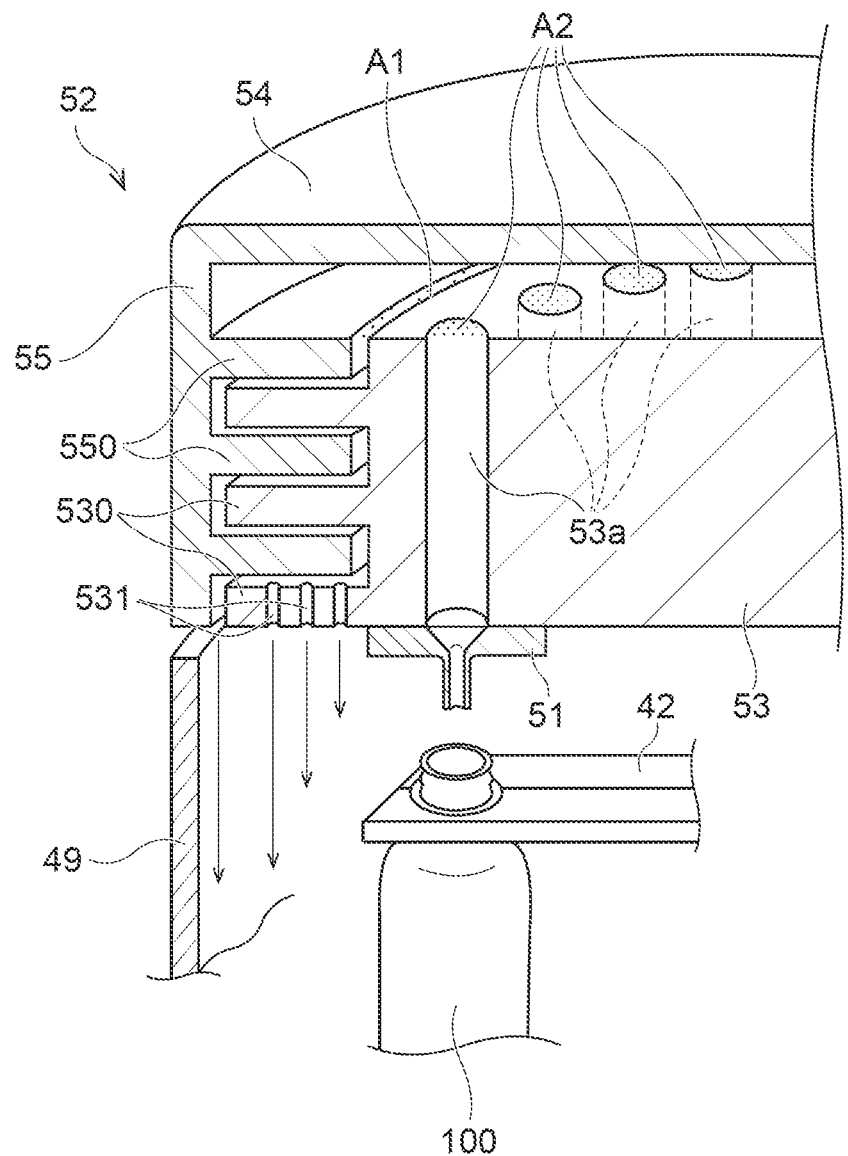
FIG. 5B is a schematic sectional view illustrating other examples of the fixed cover and the rotary plate of the container sterilizing device according to the present embodiment.

A sealing member 61 is interposed between the fixed cover 52 and the rotary plate 53. To be specific, the sealing member 61 is interposed between the side wall 55 of the fixed cover 52 and the rotary plate 53. The sealing member 61 prevents leakage of the sterilizing agent from the gap between the fixed cover 52 and the rotary plate 53. As the sealing member 61, for example, polyetheretherketone (PEEK) or Teflon (registered trademark) may be used. The sealing member 61 may be interposed between the top portion 54 of the fixed cover 52 and the rotary plate 53. If there is a possibility that the sealing member 61 wears and deteriorates, in order to prevent the sealing member 61 from entering the bottle 100, a cover 61a for preventing entry of foreign substances may be attached to the rotary plate 53. As illustrated in FIG. 4, the cover 61a may be attached to an upper part of the tunnel 49. In the illustrated example, the sealing member 61 is interposed between the fixed cover 52 and the rotary plate 53. However, the position of the sealing member 61 is not limited to this. For example, as illustrated in FIG. 5A, the sealing member 61 need not be interposed between the fixed cover 52 and the rotary plate 53. In this case, it is possible to supply sterilizing-agent gas to the outer surface of the bottle 100 through the gap between the fixed cover 52 (non-rotational body) and the rotary plate 53 (rotational body). That is, it is possible to guide the sterilizing-agent gas that has passed through the gap between the fixed cover 52 and the rotary plate 53 to the outer surface of the bottle 100. Therefore, an additional nozzle for sterilizing the outer surface of the bottle 100 is not necessary. In this case, preferably, the diameter of the tip of the nozzle 51 attached to the rotary plate 53 is smaller than or equal to a half of the diameter of the mouth of the bottle 100, and is preferably 3 mm or larger. Thus, it is possible to efficiently guide the sterilizing-agent gas that has passed through the opening 53a to the inner surface of the bottle 100. Moreover, for example, it is also possible to suppress leakage of the sterilizing agent through the gap between the fixed cover 52 and the rotary plate 53 by using a labyrinthine structure. In this case, as illustrated in FIG. 5B, the fixed cover 52 may include protruding portions 550 that protrude from the side wall 55 inward in the radial direction, and the rotary plate 53 may include protruding portions 530 that protrude outward in the radial direction. Thus, the sterilizing-agent flow path between the fixed cover 52 and the rotary plate 53 can be made to have a labyrinthine shape. In this case, the total area of a clearance A1 (dotted region in FIG. 5B) between the fixed cover 52 (non-rotational body) and the rotary plate 53 (rotational body) in a plan view may be smaller than or equal to a half of the total area of entrances A2 (dotted regions in FIG. 5B) of the openings 53a in a plan view, and preferably may be ⅕ of the total area of the entrances A2. In this case, it is possible to suppress leakage of the sterilizing agent mist or gas and to effectively introduce the sterilizing agent into the bottle 100. Moreover, in this case, one of the protruding portions 550 and 530 that is positioned nearest to the bottle 100 may have a through hole extending therethrough in the vertical direction. In the illustrated example, one of the protruding portion 530 that is positioned nearest to the bottle 100 has through-holes 531 extending therethrough in the vertical direction. Thus, it is possible to guide the sterilizing-agent gas that has passed through the gap between the fixed cover 52 and the rotary plate 53 to the outer surface of the bottle 100. Therefore, an additional nozzle for sterilizing the outer surface of the bottle 100 is not necessary.

Moreover, as illustrated in FIG. 2, a fixed shield plate 62 is interposed between the fixed cover 52 and the rotary plate 53. In the present embodiment, the fixed shield plate 62 is attached to the top portion 54 of the fixed cover 52 via an attachment member 63. The fixed shield plate 62 may be attached to the side wall 55 of the fixed cover 52.

Figure 6:
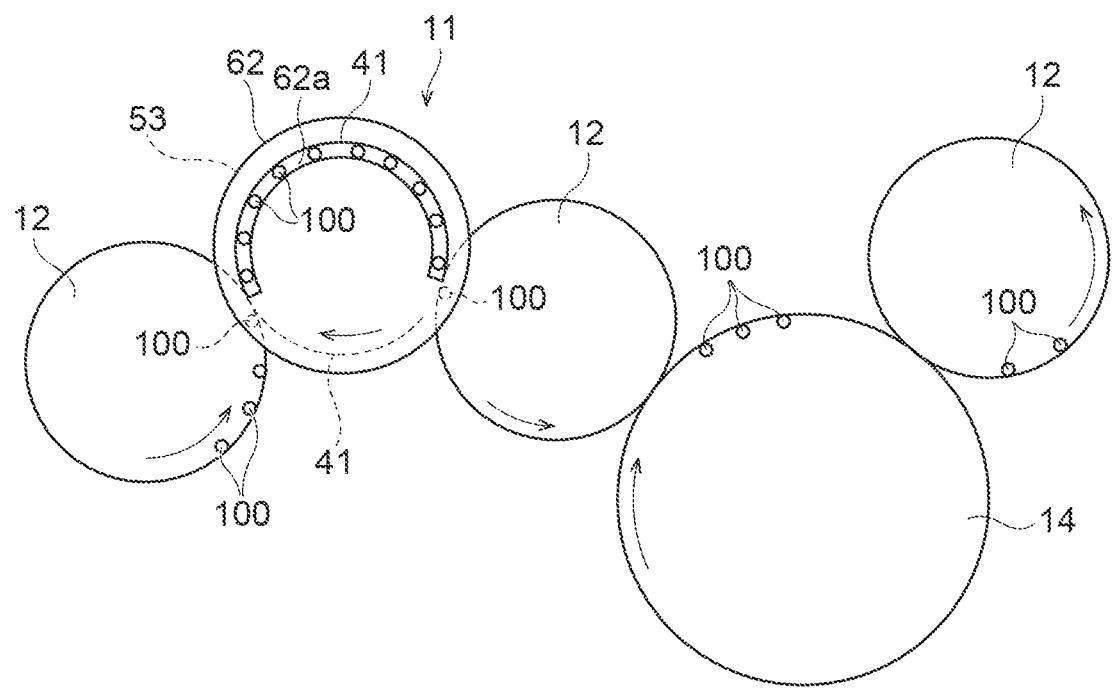
FIG. 6 is an enlarged schematic plan view illustrating the container sterilizing device according to the present embodiment.
Figure 7:
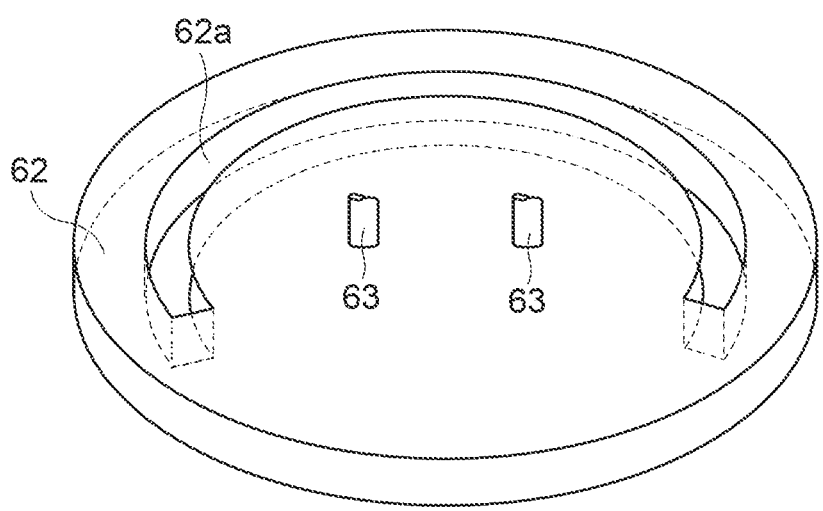
FIG. 7 is a schematic perspective view illustrating a fixed shield plate of the container sterilizing device according to the present embodiment.

As illustrated in FIGS. 2, 6, and 7, the fixed shield plate 62 has an opening 62a that is formed along the transport path of the bottle 100. In this case, as illustrated in FIGS. 6 and 7, the opening 62a has an arc shape in a plan view. The gripper 42 of the sterilizing device 11 receives the bottle 100 from the adjustment transport unit 5 on the upstream side thereof and transfers the bottle 100 to the air rinse device 14 on the downstream side thereof. Therefore, as illustrated in FIG. 6, in a plan view, there is a region where the bottle 100 passes below the rotary plate 53 and a region where the bottle 100 does not pass below the rotary plate 53 (region where the wheel 41 is shown by a broken line). Here, because the fixed shield plate 62 has the openings 62a that are formed along the transport path of the bottle 100, it is possible to effectively supply the sterilizing agent that has flowed from the inlet 52a of the fixed cover 52 to, among the openings 53a of the rotary plate 53, each opening 53a that is positioned in the region where the bottle 100 passes below the rotary plate 53. Thus, it is possible to effectively supply the sterilizing agent to, among the nozzles 51, each nozzle 51 that directly faces the bottle 100. Therefore, it is possible to efficiently spray the sterilizing agent to the bottle 100, and to reduce the amount of the sterilizing agent used. The fixed shield plate 62 may be omitted. However, if the fixed shield plate 62 is omitted, mist or gas of the sterilizing agent is sprayed from all of the nozzles 51. In this case, the sterilizing agent is sprayed from the nozzle 51 even in the region where the gripper 42 does not hold the bottle 100. Therefore, preferably, a chamber wall is provided between the wheel 41 and wheels that are disposed on both sides of the wheel 41 (in the example illustrate in FIG. 1, a wheel of the adjustment transport unit 5 and a wheel of the air rinse device 14, which are disposed on both sides of the sterilizing device 11), or the entire periphery of the wheel 41 has a tunnel structure. Thus, the chamber wall or the tunnel structure can form a space having a small volume, and the sterilizing agent can be accumulated with high concentration in the space. Therefore, it is possible to enable the sterilizing agent accumulated in the space to effectively sterilize the outer surface of the bottle 100.

Content Filling Method

Next, referring to FIG. 8, a content filling method using the content filling system 10 (FIG. 1) will be described.

Figure 8:
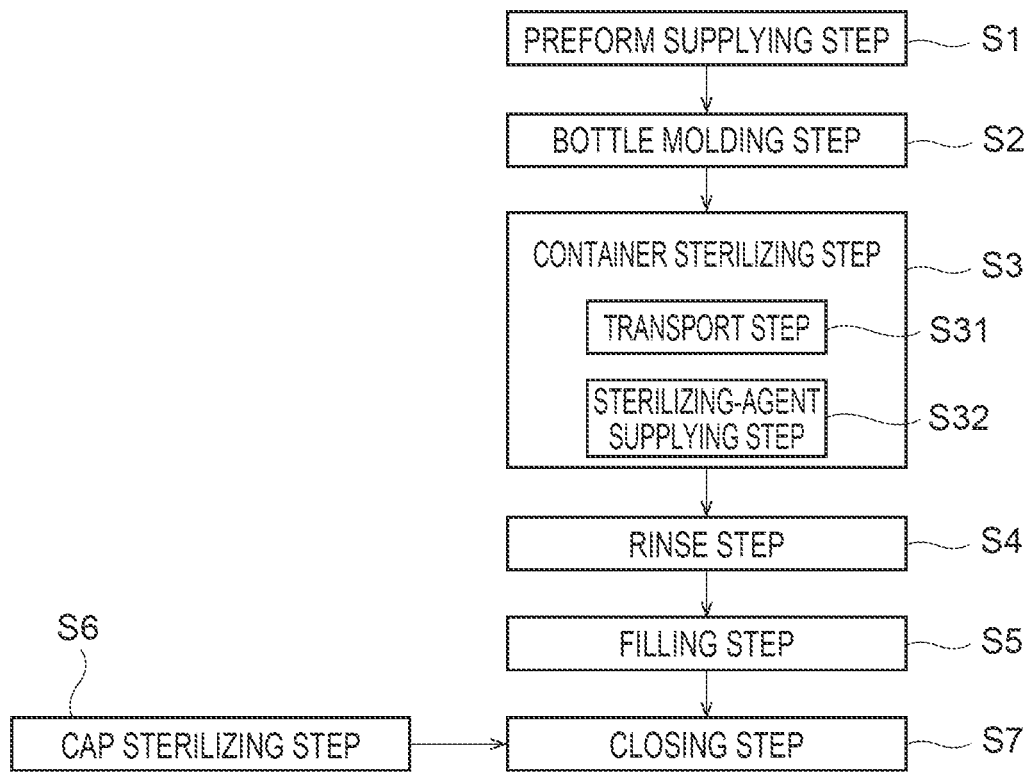
FIG. 8 is a flowchart illustrating a content filling method using the content filling system according to the present embodiment.

First, the preform supply device 1 successively supplies a plurality of preforms 100a via the preform supply conveyor 2 to the receiving portion 34 of the preform transport unit 31 (preform supplying step S1 in FIG. 8). At this time, the preform sterilizing device 34a sterilizes each preform 100a by blowing mist or gas of hydrogen peroxide to the preform 100a and dries the preform 100a with hot air.

Next, the preform 100a is supplied to the heating portion 35 and heated by the heater 35a to a temperature of, for example, about 90° C. or higher and 130° C. or lower. Next, the preform 100a, which has been heated by the heating portion 35, is supplied to the transfer portion 36. Then, the preform 100a is supplied from the transfer portion 36 to the blow molding unit 32.

Next, the bottle 100 is blow-molded by blow-molding the preform 100a, which has been supplied to the blow molding unit 32, by using a die (not shown) (bottle molding step S2 in FIG. 8). Then, the blow-molded bottle 100 is supplied to the bottle transport unit 33.

Next, the sterilizing device 11 sterilizes the bottle 100 by using hydrogen peroxide aqueous solution as a sterilizing agent (container sterilizing step S3 in FIG. 8). At this time, the hydrogen peroxide aqueous solution is gas or mist into which the solution is temporarily gasified at a temperature of the boiling point or higher, and is supplied toward the bottle 100. The mist of hydrogen peroxide aqueous solution adheres to the inner surface and the outer surface of the bottle 100, and sterilizes the inner and outer surfaces of the bottle 100.

At this time, first, the transport mechanism 40 transports the bottle 100 (transport step S31 in FIG. 8). In the present embodiment, the gripper 42, which is coupled to the wheel 41, transports the bottle 100.

Next, the supply unit 50, which has the nozzle 51 for spraying the sterilizing agent, supplies the sterilizing agent to the bottle 100 that is being transported by the transport mechanism 40 (sterilizing-agent supplying step S32 in FIG. 8).

At this time, first, the sterilizing agent flows through the conduit 56, and flows into the fixed cover 52 from the inlet 52a of the fixed cover 52. Here, the sealing member 61 (an oil seal or a V-ring) is interposed between the fixed cover 52 and the rotary plate 53. The sealing member 61 can prevent leakage of the sterilizing agent through the gap between the fixed cover 52 (non-rotational body) and the rotary plate 53 (rotational body). Thus, because the sealing member 61 is interposed between the fixed cover 52 and the rotary plate 53, it is possible to easily connect the non-rotational body and the rotational body without providing a so-called rotary joint in the supply unit 50 that supplies the sterilizing agent. Therefore, it is possible to reduce the manufacturing cost of the sterilizing device 11.

Next, the sterilizing agent, which has flowed into the fixed cover 52, passes through the opening 62a of the fixed shield plate 62, and is supplied to the nozzle 51 from the opening 53a of the rotary plate 53. Here, the opening 62a of the fixed shield plate 62 is formed along the transport path of the bottle 100 as described above. Thus, the sterilizing agent is effectively supplied to, among the openings 53a of the rotary plate 53, each opening 53a that is positioned in a region below which the bottle 100 passes. Therefore, it is possible to effectively supply the sterilizing agent to, among the nozzles 51, each nozzle 51 that directly faces the bottle 100.

Next, the sterilizing agent, which has been supplied to the nozzle 51, is supplied to the bottle 100. At this time, the nozzle 51 does not move in the vertical direction and, without being inserted into the bottle 100, supplies the sterilizing agent to the bottle 100 while moving in synchronization with the bottle 100 that is being transported by the gripper 42 of the transport mechanism 40. Thus, because the nozzle 51 does not move in the vertical direction and is not inserted into the bottle 100, it is possible to reduce the operation time for supplying the sterilizing agent. Because the nozzle 51 is not inserted into the bottle 100, even if the bottle 100 has a thin wall, it is possible to suppress deformation of the bottle 100 due to heat of the sterilizing agent.

Because the nozzle 51 moves in synchronization with the bottle 100 that is being transported by the gripper 42 of the transport mechanism 40, the nozzle 51 can supply the sterilizing agent to the bottle 100 while following the bottle 100. Thus, it is possible to efficiently supply the sterilizing agent to the inner surface of the bottle 100 and to reduce the amount of the sterilizing agent used. Because the sterilizing agent is efficiently supplied to the inner surface of the bottle 100, it is possible to heat the bottle 100 to a desirable temperature by using heat of the sterilizing agent. Therefore, it is possible to improve efficiency in sterilization of the bottle 100 without providing temperature adjusting equipment, which may be generally provided on the downstream side of the blow molding unit 32 in order to prevent thermal contraction of the bottle 100 and to improve sterilization efficiency.

In this case, if the sterilizing agent supplied into the bottle 100 is hydrogen peroxide gas, the concentration of the hydrogen peroxide gas may be, for example, 5 mg/L or larger and 50 mg/L or smaller. When the concentration of the hydrogen peroxide gas is 5 mg/L or higher, it is possible to obtain a sufficient sterilizing effect. When the concentration of the hydrogen peroxide gas is 50 mg/L or lower, it is possible to suppress increase of time for supplying hot air for removing residual hydrogen peroxide, and thus it is possible to reduce the sizes of the sterilizing device 11 and the content filling system 10. If the sterilizing agent is mist of hydrogen peroxide, the amount of the mist of hydrogen peroxide is, on a 35 mass % basis, for example, 5 µL/bottle or larger and 100 µL/bottle or smaller. When the amount of mist of hydrogen peroxide is 5 µL/bottle or higher, it is possible to obtain a sufficient sterilizing effect. When the amount of the mist of hydrogen peroxide is 100 µL/bottle or smaller, it is possible to suppress increase of time for supplying hot air for removing residual hydrogen peroxide, and thus it is possible to reduce the sizes of the sterilizing device 11 and the content filling system 10.

If the sterilizing agent is 35 mass % hydrogen peroxide, the flow rate of the sterilizing agent may be 30 L/min or higher and 400 L/min or lower, and preferably may be 50 L/min or lower and 300 L/min or lower. When the flow rate of sterilizing agent is 30 L/min or higher, it is possible to increase the efficiency in sterilization of the bottle 100. When the flow rate of sterilizing agent is 400 L/min or lower, it is possible to reduce the cost while maintaining the efficiency in sterilization of the bottle 100.

The temperature of the sterilizing agent may be 70° C. or higher and 200° C. or lower. When the temperature of the sterilizing agent is 70° C. or higher, it is possible to improve the efficiency in sterilization of the bottle 100. When the temperature of the sterilizing agent is 200° C. or lower, even if the bottle 100 has a thin wall, it is possible to suppress deformation of the bottle 100 due to heat of the sterilizing agent.

Moreover, the time for supplying the sterilizing agent may be 0.2 seconds or longer and 4.0 seconds or shorter, and preferably may be 0.5 seconds or longer and 4.0 seconds or shorter. When the time for supplying the sterilizing agent is 0.2 seconds or longer, it is possible to improve the efficiency in sterilization of the bottle 100. When the time for supplying the sterilizing agent is 0.5 seconds or longer, it is possible to effectively warm the bottle 100 by using heat of the sterilizing agent. When the time for supplying the sterilizing agent is 4.0 seconds or shorter, it is possible to reduce the operation time for supplying the sterilizing agent while maintaining the efficiency in sterilization of the bottle 100.

Next, the bottle 100 is supplied to the air rinse device 14, and the air rinse device 14 removes foreign substances, hydrogen peroxide, and the like from the bottle 100 while activating hydrogen peroxide by supplying aseptic heated air or room-temperature air. As necessary, hydrogen peroxide may be gasified by mixing condensation mist of low-concentration hydrogen peroxide with room-temperature aseptic air, and the hydrogen peroxide gas may be supplied to the bottle 100. Next, the bottle 100 is transported to the aseptic-water rinse device 15. The aseptic-water rinse device 15 performs cleaning by using aseptic water having a temperature of about 15° C. or higher and 85° C. or lower (rinse step S4 in FIG. 8). To be specific, aseptic water having a temperature of about 15° C. or higher and 85° C. or lower is supplied to the bottle 100 at a flow rate of 5 L/min or higher and 15 L/min or lower. At this time, preferably, the bottle 100 is in an inverted state, the aseptic water is supplied into the bottle 100 from the mouth facing downward, and the aseptic water flows out of the bottle 100 from the mouth. The warm water washes off hydrogen peroxide adhering to the bottle 100 and removes foreign substances.

Next, the bottle 100 is transported to the filling device 20. The filling device 20 fills the bottle 100 with a content from the mouth of the bottle 100 while the bottle 100 is rotated (revolved) (filling step S5 in FIG. 8).

The content is prepared and heat-sterilized in advance before the filling device 20 fills the bottle 100 with the content. In general, the heating temperature is about 60° C. or higher and 120° C. or lower if the pH of the content is lower than 4.0, and about 115° C. or higher and 150° C. or lower if the pH of the content is 4.0 or higher. Thus, all microorganisms that is in the content before filling the bottle with and may grow in the product bottle 101 are all killed. The content that has been heat-sterilized is cooled to a temperature of about 3° C. or higher and 40° C. or lower.

The filling device 20 fills the sterilized bottle 100 with the content that has been sterilized and cooled to room temperature. The temperature of the content during filling is, for example, about 3° C. or higher and 40° C. or lower.

Next, the transport wheel 12 transports the bottle 100, which has been filled with the content, to the cap attachment device 16.

The cap sterilizing device 18 sterilizes the cap 80 beforehand (cap sterilizing step S6 in FIG. 8). First, the cap 80 is transported from the outside of the content filling system 10 into the cap sterilizing device 18. Next, the cap sterilizing device 18 sterilizes the inner and outer surfaces of the cap 80 by blowing mist or gas of hydrogen peroxide to the cap 80, and dries the cap 80 with hot air. Then, the cap 80 is supplied to the cap attachment device 16.

Next, the cap attachment device 16 attaches the sterilized cap 80 to the mouth of the bottle 100, which has been transported from the filling device 20, to close the bottle 100, thereby obtaining the product bottle 101 (closing step S7 in FIG. 8).

Subsequently, the product bottle 101 is transported from the cap attachment device 16 to the product-bottle discharge section 22, and is discharged to the outside of the content filling system 10.

Each of the steps from the container sterilizing step to the closing step is performed in an aseptic atmosphere surrounded by the sterilizing-agent spraying chamber 70c, the first sterilizing-agent removing chamber 70d, the second sterilizing-agent removing chamber 70e, or the aseptic chamber 70f, that is, in an aseptic environment. The inside of the sterilizing-agent spraying chamber 70c, the first sterilizing-agent removing chamber 70d, the second sterilizing-agent removing chamber 70e, or the aseptic chamber 70f is sterilized beforehand by spraying of hydrogen peroxide, ejection of warm water, or the like. Then, after the sterilization, aseptic air having a positive pressure is supplied into the sterilizing-agent spraying chamber 70c, the first sterilizing-agent removing chamber 70d, the second sterilizing-agent removing chamber 70e, or the aseptic chamber 70f so that the aseptic air is constantly blown out toward the outside from the sterilizing-agent spraying chamber 70c, the first sterilizing-agent removing chamber 70d, the second sterilizing-agent removing chamber 70e, or the aseptic chamber 70f.

Preferably, the content filling system 10 produces the bottle 100 with a production (transport) speed of 100 bpm or higher and 1500 bpm or lower. Here, "bpm" (bottle per minute) refers to the transport speed of the bottles 100 per minute.

As described above, with the present embodiment, the supply unit 50 includes the nozzle 51 for spraying a sterilizing agent; and the nozzle 51 does not move in the vertical direction and, without being inserted into the bottle 100, moves in synchronization with the bottle 100 that is being transported by the transport mechanism 40. Thus, because the nozzle 51 does not move in the vertical direction and is not inserted into the bottle 100, it is possible to reduce an operation time for supplying the sterilizing agent. Because the nozzle 51 is not inserted into the bottle 100, it is possible to suppress deformation of the bottle 100 due to heat of the sterilizing agent, even if the bottle 100 has a thin wall. Moreover, a mechanism for moving the nozzle 51 in the vertical direction is not necessary in the sterilizing device 11, and the cost of the sterilizing device 11 can be reduced.

With an existing technology in which a rotary joint is used and a nozzle is inserted into a bottle, it is possible to reliably guide gas of hydrogen peroxide into the bottle while maintaining the gas concentration of hydrogen peroxide without allowing the gas to leak to the outside an aseptic chamber. However, it has been found that, provided that the hydrogen peroxide gas concentration can be maintained at a certain level or higher, it is possible to sterilize a bottle without any problem even if the hydrogen peroxide gas leaks to the outside of an aseptic chamber. With the present embodiment, because an expensive rotary joint is not necessary, it is possible to reduce the manufacturing cost of the sterilizing device 11 and to sterilize the bottle 100 without any problem.

The existing technology described above has an advantage in that a bottle having a thick wall can be efficiently warmed by inserting the nozzle into the bottle. However, because the thickness of the wall of the bottle 100 has been reduced in recent years, it has been found that it is possible to effectively warm the bottle 100 by making the time for supplying the sterilizing agent be 0.5 seconds or longer, even if the nozzle 51 is not inserted into the bottle 100. Moreover, it has been found that, by not inserting the nozzle 51 into the bottle 100, it is possible to effectively warm the mouth of the bottle 100, which is the thickest part of the bottle 100. That is, it has been found that the mouth having a thick wall is warmed and the sterilization effect is improved by spraying high-temperature hydrogen peroxide gas to the mouth of the bottle 100 from above the mouth without inserting the nozzle 51 into the bottle 100. Therefore, with the present embodiment, it is possible to improve the effect of sterilizing the mouth, because the nozzle 51 does not move in the vertical direction and, without being inserted into the bottle 100, moves in synchronization with the bottle 100 that is being transported by the gripper 42 of the transport mechanism 40.

Because the nozzle 51 moves in synchronization with the bottle 100 that is being transported by the gripper 42 of the transport mechanism 40, the nozzle 51 can supply the sterilizing agent to the bottle 100 while following the bottle 100. Thus, it is possible to efficiently supply the sterilizing agent to the inner surface of the bottle 100 and to reduce the amount of the sterilizing agent used. Because the sterilizing agent is efficiently supplied to the inner surface of the bottle 100, it is possible to heat the bottle 100 to a desirable temperature by using heat of the sterilizing agent. Therefore, it is possible to increase the efficiency in sterilization of the bottle 100 without providing temperature adjusting equipment on the downstream side of the blow molding unit 32. Because the temperature adjusting equipment is not necessary, it is possible to reduce the size and the cost of the content filling system 10, and it becomes possible to install the content filling system 10 in a space in which it has not been possible to install the content filling system 10. Moreover, because the temperature adjusting equipment is not necessary, temperature monitoring equipment for monitoring the temperature of the bottle 100 is not necessary, and it is possible to further reduce the cost of the sterilizing device 11.

The supply unit 50 includes the fixed cover 52 including the inlet 52a through which the sterilizing agent flows into the fixed cover 52, and the rotary plate 53 that holds the nozzle 51 and that is rotatably provided in the fixed cover 52; and the sealing member 61 is interposed between the fixed cover 52 and the rotary plate 53. Thus, it is possible to prevent leakage of the sterilizing agent from the gap between the fixed cover 52 (non-rotational body) and the rotary plate 53 (rotational body). Therefore, it is possible to easily connect a non-rotational body and a rotational body without providing a so-called rotary joint, and it is possible to reduce the manufacturing cost of the sterilizing device 11.

Moreover, with the present embodiment, the fixed shield plate 62 that has the opening 62a formed along the transport path of the bottle 100 is interposed between the fixed cover 52 and the rotary plate 53. Thus, it is possible to effectively supply the sterilizing agent to, among the openings 53a of the rotary plate 53, each opening 53a that is positioned in the region below which the bottle 100 passes. Therefore, it is possible to effectively supply the sterilizing agent to, among the nozzles 51, each nozzle 51 that directly faces the bottle 100. As a result, it is possible to efficiently spray the sterilizing agent to the bottle 100 and to reduce the amount of the sterilizing agent used.

In the embodiment described above, a case where a sterilizing device that performs hydrogen peroxide sterilization and warm-water sterilization is used as a container sterilizing device has been described. However, the container sterilizing device is not limited to this. For example, the container sterilizing device may be a sterilizing device that performs peracetic acid sterilization that sterilizes the inner and outer surfaces of a bottle with peracetic acid solution (or gas or mist of peracetic acid, or a combination of these) and then rinses the inner and outer surfaces with aseptic water. Alternatively, the container sterilizing device may be: a sterilizing device that uses, instead of hydrogen peroxide or ethanol, one of peracetic acid, acetic acid, pernitric acid, nitric acid, sodium hypochlorite, chlorine, sodium hydroxide, and the like as a sterilizing agent; a sterilizing device that uses only one of these as a sterilizing agent; or a sterilizing device that uses a combination of two or more of these as a sterilization agent. The sterilizing device may be used not only to sterilize a bottle but also to sterilize a preform, a cup, a pouch, a paper container, or a combination body of any of these.

In the embodiment described above, an example in which the transport mechanism 40 includes the wheel 41 that is rotatable and the gripper 42 that is coupled to the wheel 41 and that transports the bottle 100 while holding the bottle 100 has been described. However, the transport mechanism 40 is not limited to this. For example, a star wheel or a conveyor may be used as the transport mechanism 40.

Figure 9:
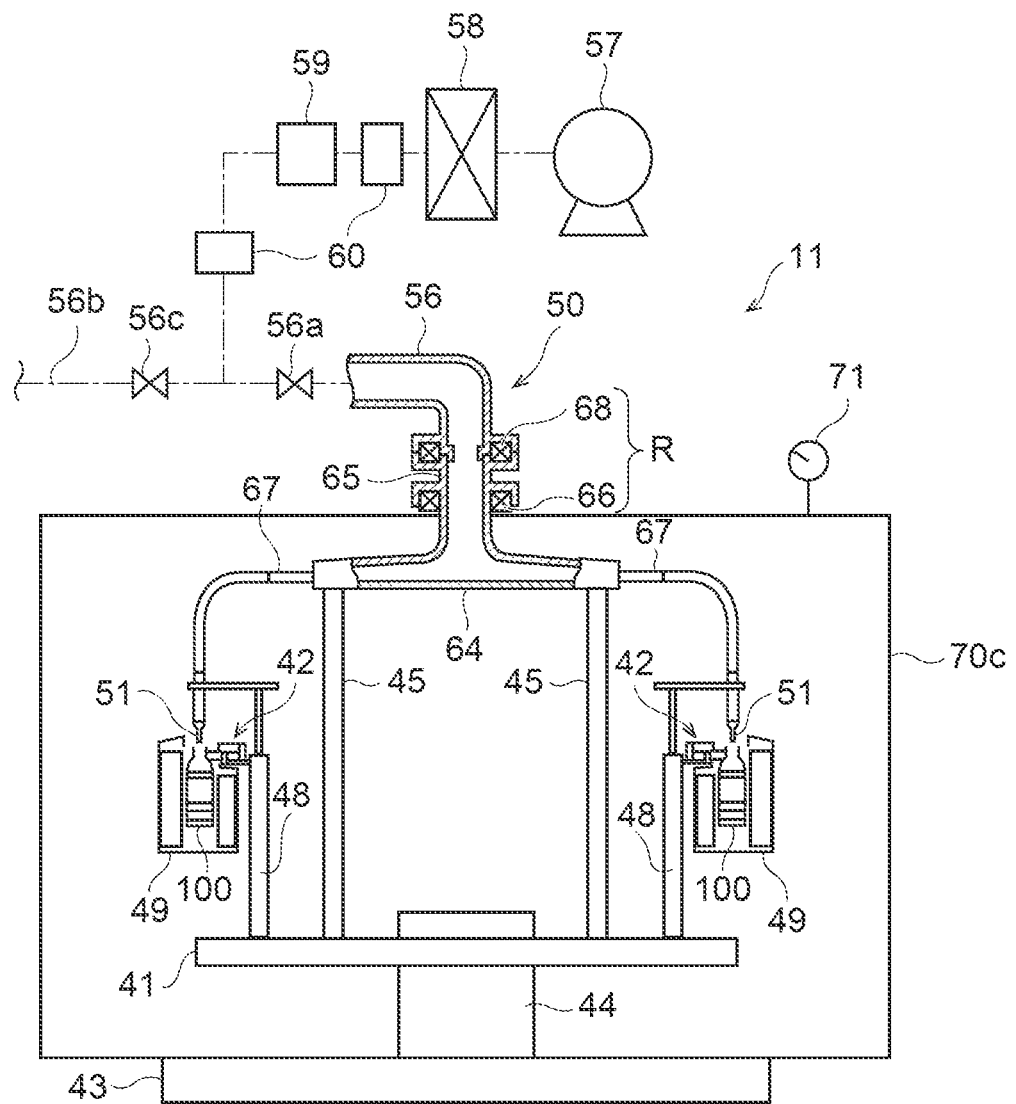
FIG. 9 is a schematic sectional view illustrating a modification of the container sterilizing device according to the present embodiment.

In the embodiment described above, a case where the sterilizing device 11 does not include a rotary joint has been described. However, the sterilizing device 11 is not limited to this. As necessary, as illustrated in FIG. 9, the sterilizing device 11 may include a rotary joint R that connects a non-rotational body and a rotational body. In this case, for example, a manifold 64, into which a sterilizing agent flows, is fixed to the upper end of the supporting poles 45. A conduit 65 extends upward from an upper central part of the manifold 64 along an extension line of the axis of the swiveling shaft 44. The conduit 65 is held by a frame member of the sterilizing-agent spraying chamber 70c, which is coupled to the base 43, via a bearing 66 that configures a part of the rotary joint R. Thus, the manifold 64 is rotatable together with the wheel 41 around the swiveling shaft 44.

Supply pipes 67 for supplying the sterilizing agent respectively extend from peripheral parts of the manifold 64 toward the grippers 42, and the nozzle 51 is attached to the tip of each of the supply pipes 67. The nozzle 51 is fixed to the supporting pole 48. Thus, as the wheel 41 rotates, the nozzle 51 rotates around the swiveling shaft 44 together with the bottle 100 held by the gripper 42 and sprays the sterilizing agent to the bottle 100.

The conduit 56 is connected to an upper end of the conduit 65, which extends upward from the manifold 64, via a seal portion 68 that configures a part of the rotary joint R. The conduit 65 rotates together with the manifold 64 relative to the conduit 56, and the seal portion 68 prevents leakage of the sterilizing agent from a connection portion where the conduits 56 and 65 are connected. Also in this case, it is possible to obtain the advantageous effects described above.

Figure 10:
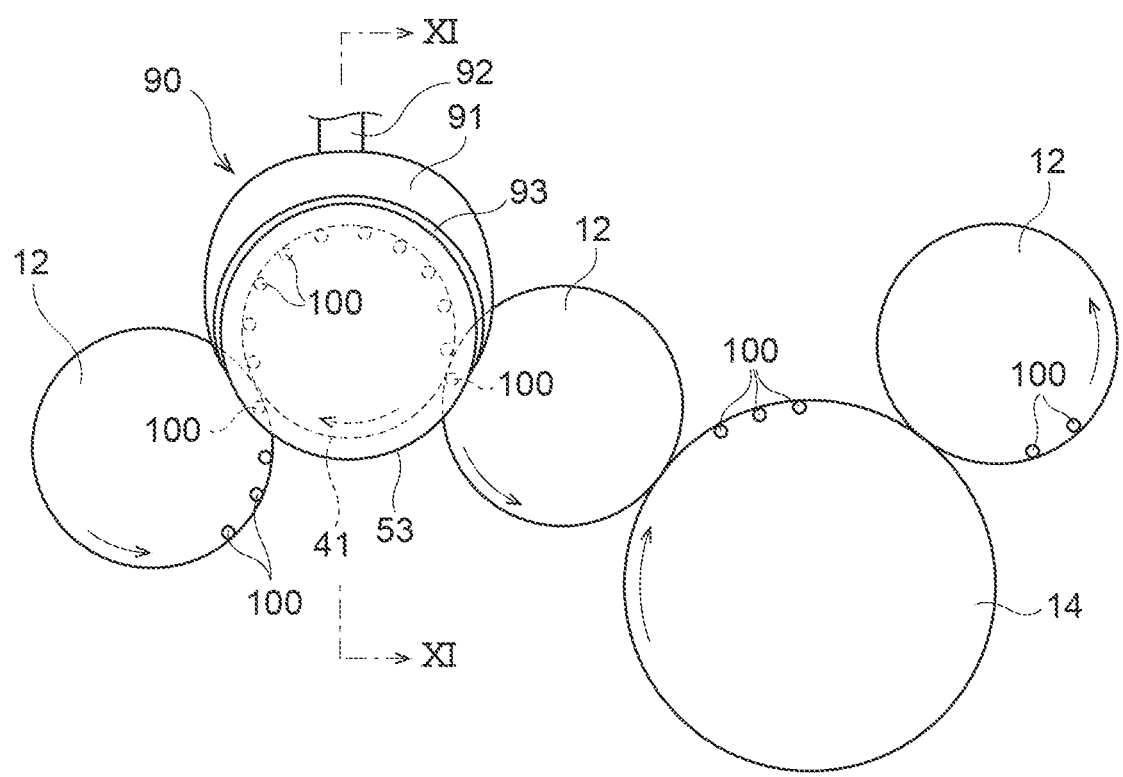
FIG. 10 is an enlarged schematic plan view illustrating a modification of the container sterilizing device according to the present embodiment.
Figure 11:
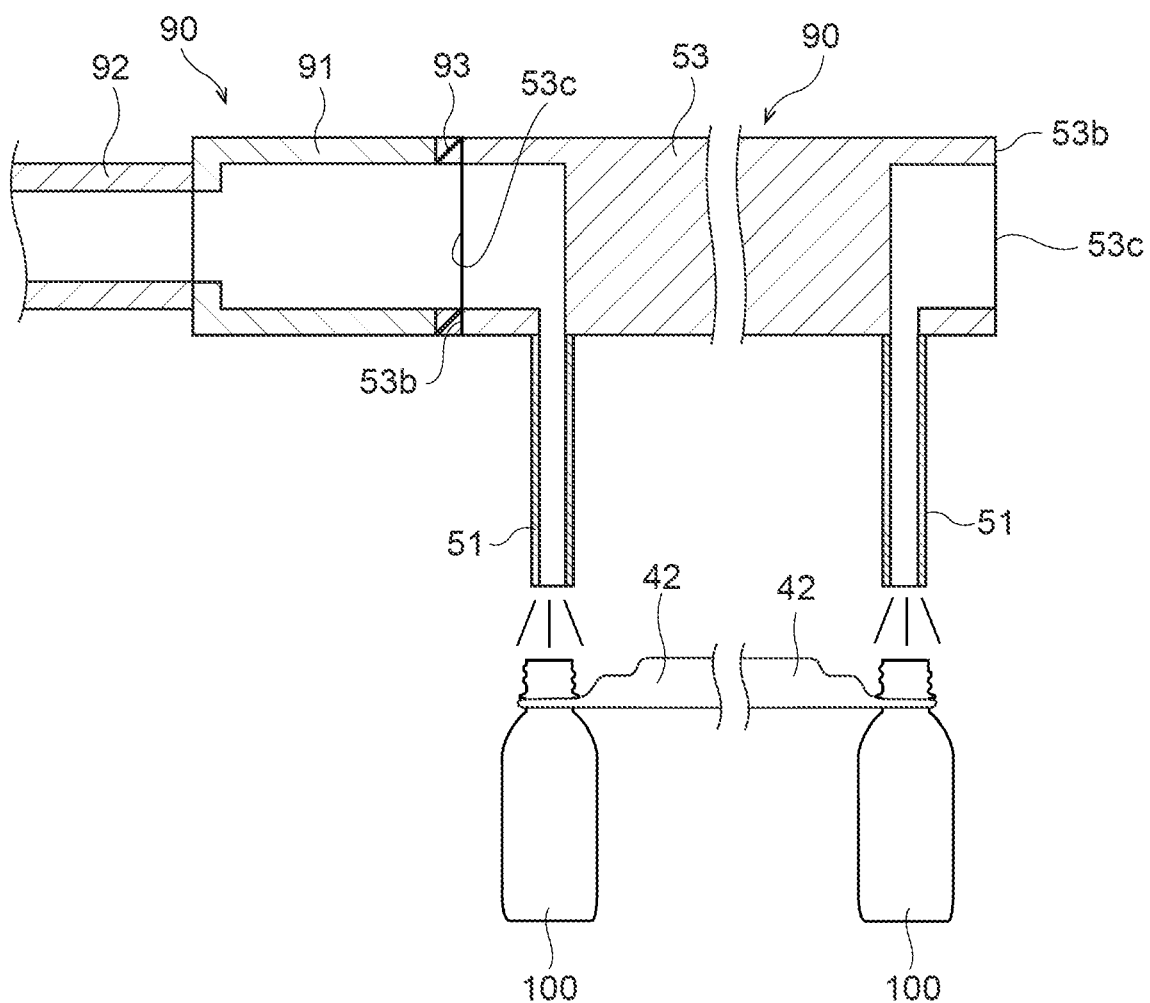
FIG. 11 is a sectional view (sectional view taken along line XI-XI of FIG. 10) illustrating a rotary plate and an auxiliary member of the modification of the container sterilizing device according to the present embodiment.

In the embodiment described above, a case where the fixed shield plate 62 that has the opening 62a formed along the transport path of the bottle 100 is interposed between the fixed cover 52 and the rotary plate 53 has been described. However, the rotary plate 53 is not limited to this. For example, as illustrated in FIGS. 10 and 11, an auxiliary member 90 for supplying the sterilizing agent may be attached to the rotary plate 53. The auxiliary member 90 includes a body 91 which is hollow and an introducing portion 92 for introducing the sterilizing agent into the body 91. The body 91 covers, among openings 53c (described below) of the rotary plate 53, each opening 53c that is positioned in a region below which the bottle 100 passes. Thus, it is possible to effectively supply the sterilizing agent to, among the openings 53c of the rotary plate 53, each opening 53c that is positioned in the region below which the bottle 100 passes. A protective member 93, for protecting the body 91 and the rotary plate 53 and improving closeness of contact with the rotary plate 53, is attached to an end of the body 91 on a side opposite to the introducing portion 92. As the protective member 93, for example, a resin material such as a fluorine resin or polyetheretherketone (PEEK) may be used.

In the present modification, the plurality of openings 53c that are arranged at intervals in the circumferential direction are formed in a side surface 53b of the rotary plate 53. The pitch of the plurality of the openings 53c is the substantially the same as the pitch the nozzle 51 so that each of the openings 53c and a corresponding one of the openings at the tip of the nozzle 51 communicate with each other as illustrated in FIG. 11.

Also with the present modification, because the body 91 of the auxiliary member 90 covers, among the openings 53c of the rotary plate 53, each opening 53c that is positioned in the region below which the bottle 100 passes, it is possible to effectively supply the sterilizing agent to, among the openings 53c of the rotary plate 53, each opening 53c that is positioned in the region below which the bottle 100 passes. Therefore, it is possible to effectively supply the sterilizing agent to, among the nozzles 51, each nozzle 51 that directly faces the bottle 100. Therefore, it is possible to efficiently spray the sterilizing agent to the bottle 100, and to reduce the amount of the sterilizing agent used.

Moreover, in the embodiment described above, a case where the content filling system 10 includes the bottle molding section 30 has been described. However, the content filling system 10 is not limited to this. For example, the content filling system may be configured to successively receive a molded empty bottle 100 from the outside and to transport the received bottle 100 toward the sterilizing device 11. Also in this case, it is possible to obtain the advantageous effects described above. In particular, if the content filling system 10 successively receives a molded empty bottle 100 from the outside, there may be a case where the bottle 100 to be sterilized by the sterilizing device 11 has released heat generated by blow molding. Also in this case, because the bottle 100 can be heated to a desirable temperature by using heat of the sterilizing agent, it is possible to improve the efficiency in sterilization of the bottle 100 without providing temperature adjusting equipment on the downstream side of the blow molding unit 32.

A plurality of constituent elements disclosed in the embodiments and the modifications described above may be combined as appropriate if necessary. Some of the constituent elements shown in the embodiments and the modifications described above may be omitted.

The invention claimed is:

1. A container sterilizing device comprising:
   a transport mechanism that transports a container; and
   a supply unit that supplies a sterilizing agent to the container that is being transported by the transport mechanism,
   wherein the supply unit includes a nozzle for spraying the sterilizing agent,
   the nozzle does not move in a vertical direction and, without being inserted into the container, moves in synchronization with the container that is being transported by the transport mechanism,
   wherein the supply unit further includes a fixed cover that includes an inlet through which the sterilizing agent flows into the fixed cover, and a rotary plate that holds the nozzle and that is rotatably provided in a gap formed by the fixed cover,
   a sealing member is interposed between the fixed cover and the rotary plate,
   wherein the sealing member contacts the fixed cover and the rotary plate preventing leakage of the sterilizing agent from the gap between the fixed cover and the rotary plate.

2. The container sterilizing device according to claim 1, wherein a fixed shield plate that has an opening formed along a transport path of the container is interposed between the fixed cover and the rotary plate.

3. A content filling system comprising:
   the container sterilizing device according to claim 1;
   a filling device that fills the container with a content; and
   a cap attachment device that closes the container with a cap.

4. A container sterilizing method comprising:
   a transport step of transporting a container by using a transport mechanism; and
   a sterilizing-agent supplying step of supplying a sterilizing agent to the container that is being transported by the transport mechanism by using a supply unit including a nozzle for spraying the sterilizing agent,
   wherein, in the sterilizing-agent supplying step, the nozzle does not move in a vertical direction and, without being inserted into the container, supplies the sterilizing agent to the container while moving in synchronization with the container that is being transported by the transport mechanism,
   wherein the supply unit includes a fixed cover that includes an inlet through which the sterilizing agent flows into the fixed cover, and a rotary plate that holds the nozzle and that is rotatably provided in a gap formed by the fixed cover,
   a sealing member is interposed between the fixed cover and the rotary plate,
   wherein the sealing member contacts the fixed cover and the rotary plate preventing leakage of the sterilizing agent from the gap between the fixed cover and the rotary plate.

5. The container sterilizing method according to claim 4, wherein a fixed shield plate that has an opening formed along a transport path of the container is interposed between the fixed cover and the rotary plate.

6. A content filling method comprising:
   a container sterilizing step of sterilizing a container by using the container sterilizing method according to claim 4;
   a filling step of filling the container with a content; and
   a closing step of closing the container with a cap.

* * * * *